US00PP09491P

United States Patent [19]

van Geest

[11] Patent Number: Plant 9,491

[45] Date of Patent: Mar. 26, 1996

[54] FICUS PLANT NAMED INDIGO

[75] Inventor: J. van Geest, JP's Gravenzande, Netherlands

[73] Assignee: The Plantenkwekerij P. Van Geest B.V., Netherlands

[21] Appl. No.: 382,363

[22] Filed: Jan. 31, 1995

[51] Int. Cl.[6] ..... A01H 5/00

[52] U.S. Cl. ..... Plt./88.9

[58] Field of Search ..... Plt./88.9

*Primary Examiner*—James R. Feyrer

*Attorney, Agent, or Firm*—Christie, Parker & Hale

[57] ABSTRACT

A Ficus plant having dark green leaf blades and a variegated lighter green irregularly shaped section on mature foliage.

2 Drawing Sheets

BACKGROUND OF THE INVENTION

The present invention comprises a new and distinct cultivar of Ficus. The varietal denomination of the new cultivar is 'Indigo'.

The new variety was discovered as a mutation in a controlled planting of *Ficus benjamina* 'Exotica' in a greenhouse in the Westlands, The Netherlands.

SUMMARY OF THE INVENTION

Ficus 'Indigo' is a distinct and new cultivar discovered as a mutation of *Ficus benjamina* 'Exotica' in a controlled planting of 'Exotica'. It differs significantly in appearance from its parent plant in that the color of the leaf blades are of a much darker green, than *Ficus benjamina* 'Exotica' and have a lighter green irregularly shaped section on the mature foliage. The irregular section appears centrally on the leaf, along the mid-rib. The overall leaf is also much thicker, harder and crisper than *Ficus benjamina* 'Exotica'. It has been observed that when 'Indigo' is maintained under low light levels, e.g. less than 3000 footcandles, it is extremely durable and capable of holding its foliage and highly resistant to leaf drop. The growth rate and growth habit closely resembles those of its parent. The new variety is also different than *Ficus benjamina* 'Monique', (U.S. Plant Pat. No. 8,637), also an *F. benjamina* mutation. 'Monique' has foliage of a much lighter green color, near 144A, and has a crenated leaf edge. 'Indigo' foliage is very dark in color, with an irregular section of lighter green coloration along the mid-rib of the leaf. 'Monique' and the 'Indigo' have leathery thick crisp leaves when compared to a *Ficus benjamina*, and both are resistant to leaf drop under stress conditions when compared to a *Ficus benjamina.*

The irregularly shaped variegation that occurs along the mid-rib of mature foliage is near 137C to 137D, on both the upper side and under side of mature leaves. There is no visible variegation on new foliage. The variegated portion does not appear on young leaves because the entire leaf color is near 144A. As the leaves mature, the color of the lamina surrounding the irregularly shaped section of variegation darkens to near 131A, as hereinafter described. The dark margins of the mature leaves become a predominate feature of the coloration of the leaves and of the overall appearance of the plant. However, the variegated area is apparent primarily under close examination, within an approximate visual range of about six feet or less. When observed from a distance of more than six feet, the overall predominate feature would appear to be an overall darker coloration.

The leaf thickness is not measurable in terms of millimeters however there is a markedly more glossy, leathery texture to the leaves of the new cultivar when compared to *Ficus benjamina* by touch or feel. The leaves of 'Indigo' are slightly more rigid than those of its parent 'Exotica'; however, the ploidy of the plant has not been determined.

The new variety has been asexually reproduced vegetatively by rooted cuttings in The Westlands, The Netherlands. Asexual reproduction through succeeding generations has established that the combination of characteristics as herein disclosed for the new cultivar is firmly fixed and is retained through successive generations of asexual reproduction.

BRIEF DESCRIPTION OF THE ILLUSTRATIONS

The accompanying illustrations show specimens of the new cultivar in photo illustrations as true to color as is reasonably possible to make in illustrations of this character. One photo describes the dark green leaf blades with irregularly shaped sections of different lighter green coloration on a mature foliage. The other photo shows the growth habit of 'Indigo'.

DESCRIPTION OF THE NEW VARIETY

'Indigo' has not been observed under all possible environmental conditions. The phenotypic expression may vary with variations in environment such as temperature, light intensity and day length. The following observations and descriptions are of plants grown under glass in the Netherlands and both outdoor and under plastic in Homestead, Fla. in June. In this description, color references are to The Royal Horticultural Society Colour Chart (R.H.S.C.C.). The terminology used in the color descriptions herein refers to plate numbers in this color chart.

Classification:

*Botanical.—Ficus benjamina* cv. 'Indigo'.

Parentage: Mutation of *Ficus benjamina* 'Exotica'.

Propagation: By vegetative cuttings and other known asexual reproduction techniques.

Habit: Upright, multiple branching woody ornamental.

PLANT

A. Form: 'Indigo''s form is upward, vertically dominant, rather irregular and richly branching, lateral branches are at a sharp angle to its trunk (approx. 45 degrees), straight but bent at the top; young stem is light green with a reddish-brown hue, near 195A, later turning light brown, near 197A.

B. Growth: Extremely vigorous with somewhat irregular branching.

*Height attained.*—1.5–3.0 meters, eight months to eighteen months old, of plants grown from rooted tip cuttings under glass in The Netherlands. Plants three meters in height have been manually maintained at that height through pruning practices so that the plants have a uniform height for commercial purposes. The parent, 'Exotica', may reach heights of 16 meters or more; however, it is not known if the new variety is capable of reaching that height.

C. Foliage: Medium-Large.

1. *Size.*—8.5 cm long by 3.5 cm wide, shade grown in Homestead, Fla. (about 5,000 footcandles). about 5.5 cm long by about 2.5 cm wide, sun grown in Homestead, Fla. (about 10,000 footcandles). 10 cm long by about 4 cm long, observed growing under glass in The Netherlands. (about 3,000 footcandles). Size of the foliage and light levels are given so that it may be noted that the size of the foliage may vary depending on light intensity under which 'Indigo' is grown.
2. *Quantity.*—Multiple, numerous. Plants of the new variety grown outdoor under shadecloth in Florida during the month of June exhibit internodal length in the range of about 22 to 28 mm on average. Internodal length varies generally within this range and branching is irregular. However, internodal lengthening has been observed on specimens grown under lower light intensities, i.e., less than 5000 fc. Internode lengths of 35 to 40 mm have been observed on specimens grown under glass at about 3000 fc in The Netherlands.
3. *Color.*—The leaf color is the most distinguishing characteristics of 'Indigo', see prior description of leaf coloration. The color is such dark green as to have been described by others as being almost blue-black. New foliage — upper side — near 141B to 141C Under side — near 141B to 141C Old foliage — upper side — near 131A Under side — near 139 to 131B The color of the foliage does not seem to have a significant variance when compared to specimens grown under varying light levels when other factors, such as nutrition, water availability and humidity levels remain constant.
4. *Shape.*—Ovate- with an acuminate leaf tip and slightly coarsely sinuate.
5. *Texture.*—Smooth and glabrous, quite highly glossy, and slightly leathery. Underside texture is smooth, with an absence of gloss.
6. *Veination.*—A single mid-rib vein running from petiole to leaf tip, convex on the under side of the leaf, and light yellow green in color. (near 145D).
7. *Edge.*—Leaf edge is smooth, and slightly undulated. The undulation is accentuated on the leaves when the plant is grown under low light conditions, about 3,000 footcandles or less. Undulation is almost absent on specimens grown outdoor, under full sun, during the month of June in Homestead, Fla.
8. *Serration.*—None.
9. *Petiole.*—About 1.5 to 2.0 cm long, light to medium Yellow–green. Color top near 147C Underside near 147C.
10. *Stipules.*—Absent.
11. *Auricle.*—Absent.
12. *Rachis.*—Absent, to date 'Indigo' fruit and flowers have not been observed.
13. *Disease resistance.*—'Indigo' is very hearty and resistant to anthracnose, *Agrobacterium radiobacter, tumefaciens*, and *Heterodera flcl.* Under stress conditions, very resistant to leaf drop. Exceptionally resistant to leaf drop when compared to *Ficus benajmina.* 'Indigo' is susceptible to mites, thrips, mealy bug and scale, as is *Ficus benajmina.*

D. Wood:

*New shoots.*—Color medium brown, near 200D; bark is smooth.

*Old wood.*—Color lighter brown, near 199A; bark is smooth.

E. Winter hardiness: Can withstand cool temperatures to about 2° C. preferred growing temperature range is about 20° C. to 32° C.

F. Reproductive organs: Reproductive organs have not been observed to date and are not a significant feature. Indigo has been reproduced asexually, from cuttings and tissue culture in The Netherlands, and by cuttings in Homestead, Fla.

G. Uniqueness: Indigo is a unique cultivar of *Ficus benajmina*, with distinct foliage color. 'Indigo' has been described as having almost a blue-black appearance. The actual dark green color is blue-green-black. In addition, there us a lighter green irregular section along the mid rib of the leaf. Its ability to thrive under lower light levels, (less than about 2,000 lux), as well as growing well under the high tropical light levels of South Florida, set 'Indigo' into a class of Ficus well suited for commercial use for the interiorscape markets, as well as the tropical or subtropical landscape.

I claim:

1. A new and distinct cultivar of *Ficus benjamina* named 'Indigo', substantially as illustrated and described.

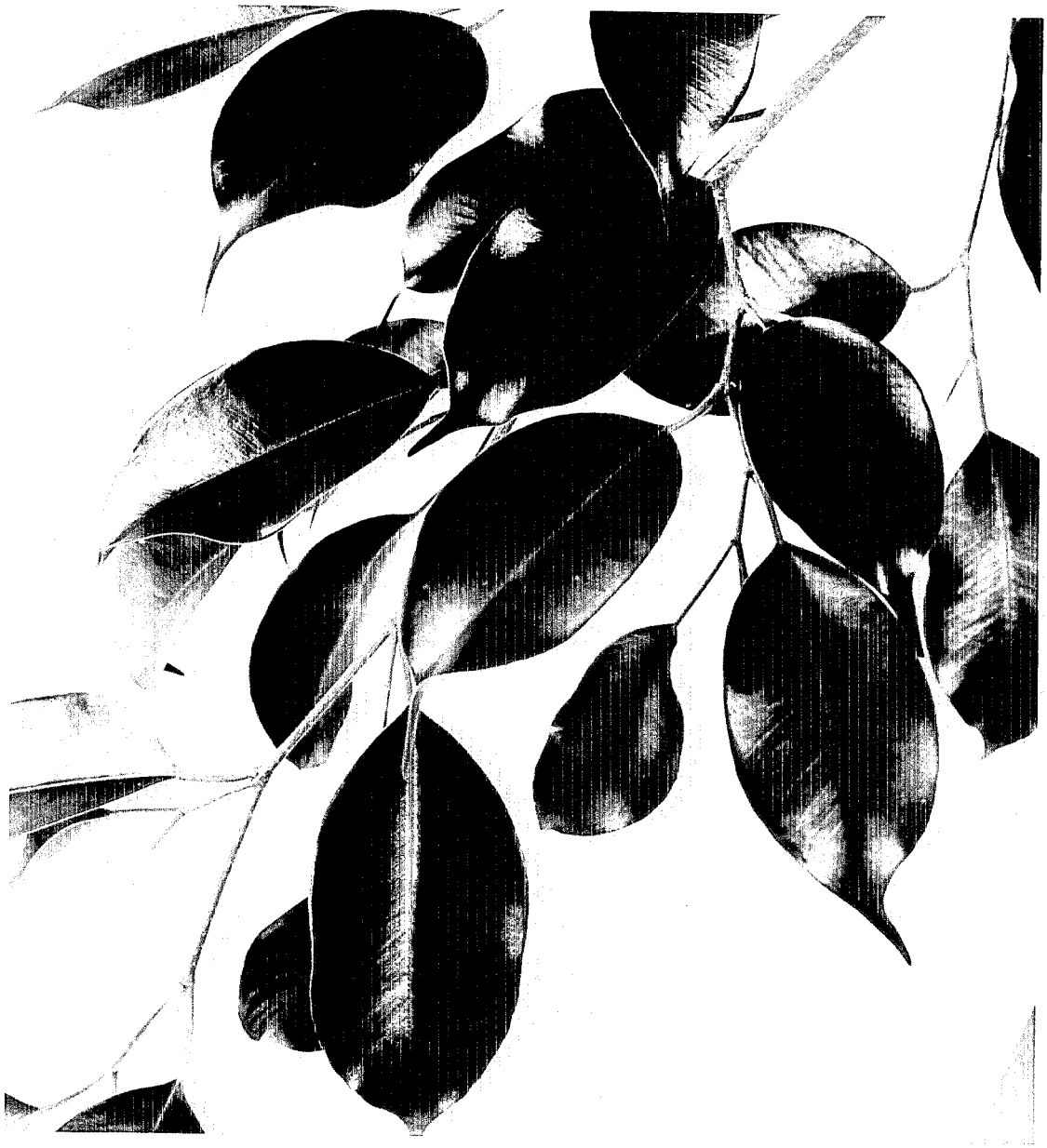

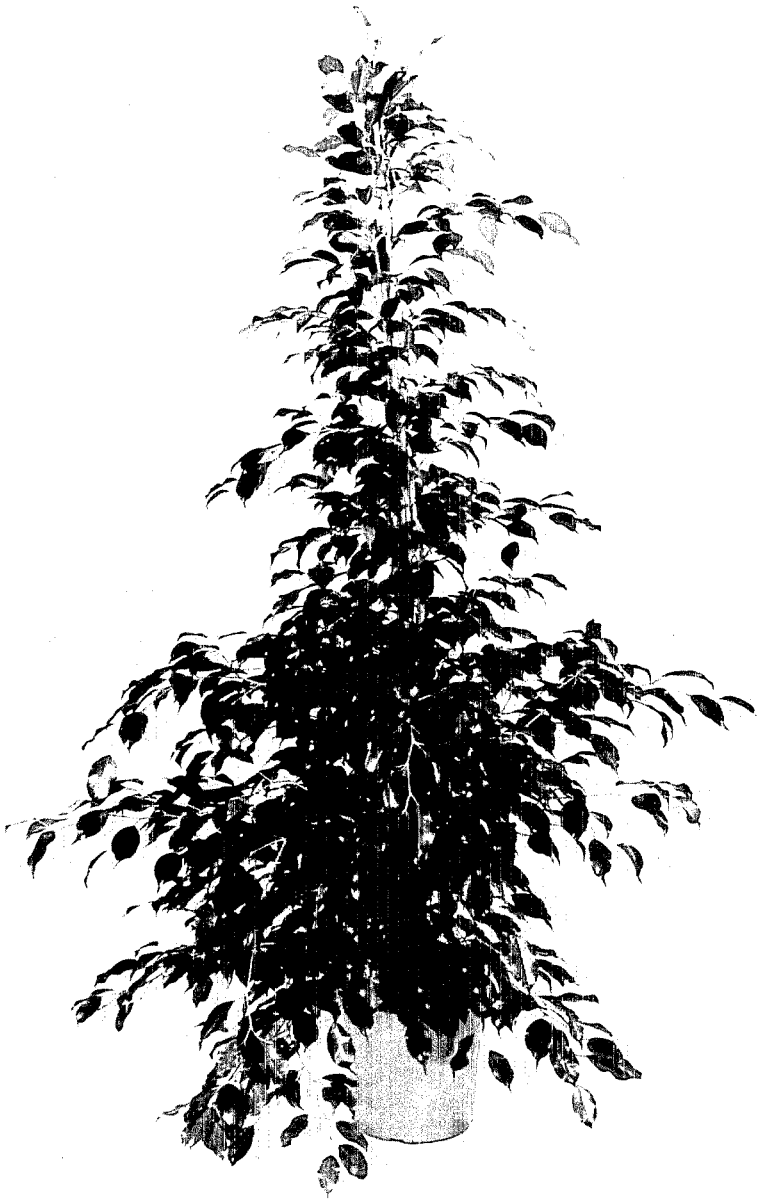

* * * * *